United States Patent [19]

Belfort

[11] Patent Number: 4,981,791

[45] Date of Patent: Jan. 1, 1991

[54] RNA STABILIZATION VECTOR

[75] Inventor: Marlene Belfort, Slingerlands, N.Y.

[73] Assignee: Health Research Incorporated, Albany, N.Y.

[21] Appl. No.: 211,594

[22] Filed: Jun. 27, 1988

[51] Int. Cl.$^5$ .................. C12P 21/00; C12N 15/00
[52] U.S. Cl. .................. 435/69.1; 455/71.2; 455/172.3; 455/320; 935/6
[58] Field of Search .......... 435/68, 91, 172.1, 172.3, 435/252.3, 252.31–252.35, 320, 69.1, 71.1, 71.2; 935/6, 27, 31, 34, 38

[56] References Cited

PUBLICATIONS

Waring et al.; Cell 40:371 (1985).
Price et al., Science 228:719 (1985).
Hall et al.; Cell 48:63 (1987).
Breathnach and Chambon, Ann. Rev. Biochem. 50, 349 (1981).
Chu et al., Proc. Natl. Acad. Sci. U.S.A. 81, 3049 (1984).
Ehrenman et al., Proc. Natl. Acad. Sci. U.S.A. 83, 5875 (1986).
Belfort et al., Cell 41, 375 (1985).
Belfort et al., Cold Spring Harbor Symp. Quant. Biol. 52, 181 (1987).
Shub et al., Proc. Natl. Acad. Sci. U.S.A. 85, 1151 (1988).
Michel and Dujon, EMBO J. 2, 33, (1983).
Cech, Cell 44, 207 (1986).
Hensgens et al., J. Mol. Biol. 164, 35 (1983).
Morelli and Macino, J. Mol. Biol. 178, 491 (1984).
Donovan and Kushner, Proc. Natl. Acad. Sci. U.S.A. 83, 120 (1986).
Gorski et al., Cell 43, 461 (1985).
Wong and Chang, Proc. Natl. Acad. Sci. U.S.A. 83, 3233 (1986).
Duvoisin et al., Gene 45, 193 (1986).
Brosius et al., Proc. Natl. Acad. Sci. U.S.A. 81, 6929 (1984).
Chu et al., Cell 45, 157 (1986).
M. J. Sleigh, Analyt. Biochem. 156, 251 (1986).
Chandry and Belfort, Genes and Development 1, 1028 (1987).

*Primary Examiner*—James Martinell
*Attorney, Agent, or Firm*—Curtis, Morris & Safford

[57] ABSTRACT

The present invention provides an RNA stabilization vector including a cloning vehicle, a group I intron inserted into the cloning vehicle and foreign DNA inserted into the intron. The present invention further provides a method for enhancing the production of a gene product by stabilizing the mRNA coding for the gene product using the RNA stabilization vector.

15 Claims, No Drawings

RNA STABILIZATION VECTOR

The invention described herein was made with the support of the Federal Government and the Federal Government has certain rights in the invention.

FIELD OF THE INVENTION

The present invention relates to methods for enhancing production of gene products by stabilizing messenger ribonucleic acid (mRNA) coding for the amino acid sequences of such products. Further, the present invention relates to a recombinant vector which contains deoxyribonucleic acid (DNA) sequences inserted into such a vector, which sequences code for stabilized mRNA for enhanced production of protein products.

BACKGROUND OF THE INVENTION

As is well known in the art, genetic information is encoded in the structure of DNA molecules (genes). Expression of the encoded information involves a two-part process. In a process known as transcription, mRNA is synthesized from the DNA template. The mRNA carries the genetic code transcribed from that DNA to specialized complexes within a living cell known as ribosomes. In a subsequent process known as translation, the cell's ribosomes "read" the mRNA "message" to produce a protein composed of a sequence of amino acids corresponding to the sequence of base pairs present in the mRNA. The resulting protein is the gene product coded by that DNA and mRNA.

It is also known that eukaryotic genes commonly contain coding regions, called exons, interrupted by non-coding regions, called intervening sequences or introns. It has been found that the RNA molecules transcribed from such "split" genes containing introns are longer than the mRNAs that subsequently produce the protein specified by the gene. Thus, by a process called splicing, the introns are excised from the newly synthesized, split precursor transcript and the exons are ligated together to form an unbroken fully-coding mRNA (Breathnach and Chambon, Ann. Rev. Biochem. 50, 349 [1981]).

There are also a few reports of introns within prokaryotic DNA, but split genes are relatively rare in bacterial species. The thymidylate synthase (td) gene of bacteriophage T4 was the first prokaryotic protein-coding gene shown to have an intervening sequence (Chu et al., Proc. Natl. Acad. Sci. USA 81, 3049 [1984]). The configuration of the td gene of bacteriophage T4 containing a 1 kilobase (kb) intron is disclosed by Chu et al., Proc. Natl. Acad. Sci. USA 81, 3049 (1984). Additional reports have characterized the intron and demonstrated that the intron is excised by a mechanism analogous to a eukaryotic group I splicing pathway (Ehrenman et al., Proc. Natl. Acad. Sci. USA 83, 5875 [1986]). The excised intron apparently circularizes and is stable, as observed by agarose gel electrophoresis (Belfort et al., Cell 41, 375 [1985]). The structure of the intron of the td gene of bacteriophage T4 is disclosed by Belfort et al., Cold Spring Harbor Symp. Quant. Biol. 52, 181 (1987) and Shub et al., Proc. Natl. Acad. Sci. USA 85, 1151 (1988).

Eukaryotic group I introns are classified into a separate group based on the distinctive secondary structure that the intron RNA can adopt (Michel and Dujon, EMBO J. 2, 33 [1983]). Many eukaryotic group I introns can splice in the absence of proteins and can therefore be excised in heterologous bacterial cells (Cech, Cell 44, 207 [1986]). The td intron of phage T4 is a group I intron, capable of self-splicing and able to be folded into a typical group I structure. Two other phage T4 introns have similar properties (Shub et al., Proc. Natl. Acad. Sci. USA 85, 1151 [1988]). It is this RNA secondary structure that is likely to impart stability to these group I intron RNAs in Escherichia coli (E. coli).

Stable excised introns have been reported in at least two eukaryotic systems. In yeast there are five mitochondrial introns reported to be stable after excision. In Saccharomyces cerevisiae, introns I1, I2, and I5 of the cytochrome oxidase subunit I gene and intron I1 of the cytochrome b gene exist in a circular form after excision and are stable (Hensgens et al., J. Mol. Biol. 164, 35 [1983]). In Neurospoa crassa, intron I2 of the ATPase subunit 6 gene exists in a circular form after excision and is stable (Morelli and Macino, J. Mol. Biol. 178, 491 [1984]).

A major aspect of recombinant DNA technology is the production in maximal practical quantities (overproduction) of medically, agriculturally or commercially useful protein products in host cells. Briefly, a foreign gene that codes for an important protein is isolated, often by the use or restriction enzymes. The term "foreign" gene designates exogenous DNA that codes for polypeptides not ordinarily produced by the host cell into which the exogenous DNA is placed.

First, the foreign gene is inserted into a cloning vehicle to form a recombinant hybrid. Preferably, a bacterial cloning vehicle is used. A bacterial cloning vehicle is a plasmid or bacteriophage replicon adapted for insertion of foreign DNA. Other cloning vehicles such as those that replicate autonomously in eukaryotic microorganisms, particularly yeast, can be used.

Next, the recombinant hybrid is introduced into the host cell, preferably a bacterial cell such as an E. coli cell. The foreign gene uses the cell machinery to express the protein for which it codes by producing mRNA which subsequently acts as the template for protein production.

There are a number of mechanisms that cells use to regulate the rate of protein synthesis. One such mechanism is the rapid breakdown of mRNAs. Bacterial mRNAs typically have a half-life value of only two minutes.

Despite the fact that a number of techniques are known to the current state of the art for enhancing production of useful gene products in host cells, there is considerable need for further improvements. Consequently, much effort has been expended in developing means for stabilizing the mRNA that produces the protein of interest in order to increase product yields.

For example, Donovan and Kushner, Proc. Natl. Acad. Sci. USA 83, 120 (1986), describe the isolation of E. coli mutants that are defective in ribonucleases that degrade mRNA. Gorski et al., Cell 43, 461 (1985) describe the alteration of the "beginning" (5' leader end) of the mRNA to stabilize the mRNA. Wong and Chang, Proc. Natl. Acad. Sci. USA 83, 3233 (1986) describe the alteration of the "end" (3' end) of the mRNA to stabilize the mRNA. These methods each stabilize the mRNA by a factor of about two to three.

The development of an expression vector based on RNA stabilization has been described (Duvoisin et al., Gene 45, 193 [1986]). However, the stabilization effect is observed only in phage T4-infected cells, making the system very cumbersome. It is well known that phage T4-infected cells lyse and are therefore unable to provide sustained production of useful products.

It can thus be readily appreciated that provision of an RNA stabilization vector that is fully functional in uninfected cells and provides a level of product amplification higher than that provided by the prior art would be a highly desirable advance over the current state of the art in recombinant technology.

OBJECTS OF THE INVENTION

It is therefore an object of this invention to provide a method of enhancing the production of protein products by recombinant technology.

It is a second object of this invention to provide a means for forming stabilized mRNA and therefore increasing its abundance in a host cell.

It is an additional object of this invention to provide a recombinant vector which stabilizes mRNA transcribed from foreign DNA inserted into such a vector for enhanced production of protein products encoded by that DNA.

It is a further object of this invention to provide methods for the over-production of proteins by stabilizing mRNA from which such proteins are translated.

These and other objects and advantages of the present invention will become more readily apparent after consideration of the following.

STATEMENT OF THE INVENTION

In one aspect, the present invention is directed to an RNA stabilization vector including at least a cloning vehicle, a group I intron inserted into the cloning vehicle and foreign DNA inserted into the intron. Surprisingly, the intron inserted into the cloning vehicle of the RNA stabilization vector stabilizes the mRNA transcribed from the foreign DNA inserted into the intron for over-production of protein products encoded by that DNA.

As is known in the art, successful expression of an inserted DNA sequence in a cloning vehicle requires two conditions. First, the insertion must be into a nonessential region of the vehicle in order that the vehicle remain viable. Second, the inserted DNA must be placed in proper proximal and transcriptional alignment downstream to a promoter, preferably a strong, regulatable promoter.

It is believed that the foreign gene inserted into the group I intron in the cloning vehicle of the RNA stabilization vector is transcribed in a host cell to form a stabilized foreign gene-intron RNA fusion. The intron sequences flanking the mRNA of the foreign gene in the foreign gene-intron RNA fusion stabilize the mRNA of the foreign gene. The half-life and abundance of the mRNA of the foreign gene in the host cell are increased. Such stabilized mRNA provides enhanced production of protein products encoded by the foreign DNA inserted into the intron in the RNA stabilization vector. Routinely, 4 to 8 fold increases of protein product yields are achieved with the RNA stabilization vector over control constructs containing the same promotor but lacking the intron stabilization sequences.

Thus, in another of its aspects, the present invention is directed to a method for enhancing the production of a gene product by stabilizing the mRNA coding for the gene product in an RNA stabilization vector. The mRNA is stabilized by inserting a foreign gene coding for the gene product into a group I intron in a cloning vehicle. The intron with inserted foreign gene is transcribed in a host cell to form a stabilized foreign gene-intron RNA fusion. The stabilized foreign geneintron RNA fusion is translated in the host cell to form the gene product of the foreign gene with improved yields.

DESCRIPTION OF PREFERRED EMBODIMENTS

The present invention, as well as other objects and features thereof, will be understood more clearly and fully from the following description of certain preferred embodiments of the invention.

The RNA stabilization vector according to the present invention is based on a cloning vehicle. Preferably, a bacterial cloning vehicle is used. Any plasmid or bacteriophage suitable for expression of inserted DNA in a host cell is advantageously used as the bacterial cloning vehicle. Examples of appropriate commercially available plasmids are pUC9, pKK223-3, pTZ18U and pBSM13. Other cloning vehicles, such as plasmids that replicate in eukaryotic microorganisms, particularly yeast, can be used.

For successful expression of inserted DNA, a suitable promoter must be located upstream from and in proper relationship to the inserted DNA sequence to be expressed.

Because of its strong regulatable promoter and termination signal, plasmid pKK223-3 is preferably used. The regulatable promoter and termination signal of pKK223-3 assure a high-level and precise synthesis of the mRNAs that are expressed. Plasmid pKK223-3 is described in Brosius et al., Proc. Natl. Acad. Sci. USA 81, 6929 (1984).

The RNA stabilization vector according to the present invention also includes group I intron DNA. Such intron DNA can be inserted into the cloning vehicle by known recombinant techniques. The td intron of bacteriophage T4 is advantageously used as the group I intron.

RNA stabilization vectors based on a modified td intron construct or stable group I introns of other genes (unmodified or modified) are also encompassed by the present invention.

For example, the intron DNA is advantageously engineered to make the RNA stabilization vector more receptive to the further insertion of foreign DNA into the intron. In particular, sequences can be deleted from the intron DNA or the intron DNA can be engineered to contain a different restriction enzyme site to facilitate insertion of foreign DNA into the intron.

Exon sequences of the corresponding modified or unmodified intron-containing gene may flank the intron. The newly synthesized RNA would then contain respectively an upstream exon, an upstream portion of the intron, the foreign RNA, a downstream portion of the intron and a downstream exon.

According to the present invention, a foreign DNA gene coding for a useful gene product is inserted by known recombinant techniques into the intron sequence inserted into the cloning vehicle of the RNA stabilization vector. The transcription product of the RNA stabilization vector in a host cell is a stabilized foreign gene-intron RNA fusion. Surprisingly, the intron sequences flanking the mRNA of the foreign gene in the foreign gene-intron RNA fusion stabilize the mRNA of the foreign gene. Such stabilized mRNA provides overproduction of gene products encoded by the foreign DNA inserted into the intron sequence of the RNA stabilization vector. Routinely, 4 to 8 fold increases of protein product yields are achieved by the present invention over control constructs that lack stabilization sequences.

Since the mRNA of the foreign DNA is stabilized because of the intron sequences flanking the foreign insert, the RNA stabilization vector will amplify the product yield of any foreign DNA sequence cloned into the intron sequence of the RNA stabilization vector.

A better understanding of the present invention and of its many advantages will be had from the following examples, given by way of illustration. Unless otherwise noted, all standard recombinant DNA manipulations were performed using procedures described in "Molecular Cloning: A Laboratory Manual" by T. Maniatis, E. F. Fritsch and J. Sambrook (1982) Cold Spring Harbor Laboratory, NY. These procedures include transformation, selection of plasmid transformants by ampicillin and, where appropriate, chloramphenicol selection, restriction enzyme analyses, DNA fragment purification, ligation, and polymerase fill-in reactions. The td sequence on which the cloning manipulations are based is provided in Chu et al., Proc. Natl. Acad. Sci. USA 81, 3049 (1984) and Chu et al., Cell 45, 157 (1986).

EXAMPLE 1

CONSTRUCTION OF RECOMBINANT VECTOR RSV1

The td gene of bacteriophage T4, described above, was ligated into a commercially available plasmid, pUC9, which had been cleaved with EcoRI. The resulting plasmid was designated pUC-Td. pUC-Td has a 2.85 kb EcoRI fragment containing the entire td gene in the EcoRI site of pUC9.

To reduce the size of the 1 kb intron of the inserted td gene of bacteriophage T4 and provide the vector with a convenient cloning site, pUC-Td was partially digested with AhaIII. Unit-length linear fragments were isolated and recircularized via XbaI linkers (5'-CTCTAGAG-3') to generate plasmids containing single XbaI linker insertions.

Those plasmids that had acquired XbaI linkers within the intron were used to make intron deletions. By ligating together (via their XbaI ends) one fragment in which the linker was near the 5' end of the intron with one in which the linker was near the 3' end of the intron, a central intron deletion of 631 basepairs (bp) was created, with an 8 bp XbaI linker at the deletion joint. This intron construction is designated tdΔ1-3 and is described by Belfort et al., Cold Spring Harbor Symp. Quant. Biol. 52, 181 (1987). The resulting vector was designated pUC-tdΔ1-03 or RSV1.

EXAMPLE 2

CONSTRUCTION OF RECOMBINANT VECTOR RSV2

The tdΔ1-3 intron construction was transferred into plasmid pKK223-3 in transcriptional alignment with ptac, creating a new vector designated pKK223-3-tdΔ1-3 or RSV2. This was achieved by cloning a 2 kb EcoRI-HpaI td fragment, containing intact exons, from RSV1 into the EcoRI-SmaI interval of pKK223-3.

EXAMPLE 3

CONSTRUCTION OF RECOMBINANT VECTORS RSV2-CAT-A AND RSV3

The chloramphenicol acetyl transferase (CAT) gene was inserted into the XbaI site of pKK223-3-tdΔ1-3 (RSV2). The 0.8 kb HindIII fragment containing the CAT gene (obtained from Pharmacia PL) was cloned via synthetic XbaI-SmaI-HindIII adaptor

5'-CTAGACCCGGGA-3'
3'-TGGGCCCTTCGA-5'.

This was achieved by a three-way ligation between XbaI-cleaved RSV2, the HindIII CAT fragment and the adaptor. Recombinants were selected on the basis of their chloramphenicol resistance (25 μg/ml). Since the CAT fragment does not have its own promoter, selection for CAT production by resistance to chloramphenicol selects for clones with the CAT fragment in transcriptional alignment with ptac.

The resulting construct was designated RSV2-CAT-A. This construct was further engineered by digestion with SmaI and elimination of the CAT fragment for production of a more general-use vector (RSV3). RSV3, which is chloramphenicol sensitive, has both SmaI and XbaI cloning sites within the intron.

EXAMPLE 4 CONSTRUCTION OF RECOMBINANT VECTOR RSV2-CAT-B

The CAT gene was inserted into the XbaI site of pKK223-3tdΔ1-3 (RSV2). The HindIII fragment containing the CAT gene was filled in with Klenow polymerase and the four deoxynucleotide triphosphates, ligated to XbaI linkers (5'-CTCTAGAG-3') and cloned into the XbaI site of RSV2. The resulting construct was designated RSV2-CAT-B. This construct was found to be an advantageous over-producer of CAT.

EXAMPLE 5 OVER-PRODUCTION OF CAT

The CAT tester fragment was cloned directly next to the ptac promoter in vector pKK223-3 to create a control construct. Thus, expression of the CAT gene in the control construct and in RSV2-CAT-B was regulated by the identical promoter in pKK223-3, the only difference in the control construct and RSV2-CAT-B being the intron sequences flanking the CAT gene in RSV2-CAT-B.

CAT activity was measured in protein extracts of the RSV2-CAT-B construct and the control as described by M. J. Sleigh, Analyt. Biochem. 156, 251 (1986). Cells were grown to mid log phase at 37° C. in L broth. Extracts were made at the indicated times after transcriptional activation (with 2 mM isopropyl-β-thiogalactoside [IPTG]at time=zero) by sonic disruption of the cells. Clarified extracts were used to determine both CAT activity and protein concentration. The data (Table I) show an 8-fold increase in CAT activity over control levels 1 hour post-induction. RNA decay kinetics show that the increase in CAT production is due to an increase in CAT mRNA stability (see also Example 9 below).

TABLE I

CAT Activity Post-Induction

| Time (in hours) | Relative CAT-Specific Activity (cpm/μg protein × 10⁻³) | |
|---|---|---|
| | RSV2-CAT-B | CONTROL |
| 0 | 1.4 | — |
| 0.5 | 12.0 | 3.2 |
| 1 | 30.9 | 3.5 |
| 2 | 39.7 | 11.8 |
| 3 | 55.2 | 18.3 |
| 4 | 99.4 | 22.6 |

EXAMPLE 6 TEMPERATURE DEPENDENCE OF CAT OVERPRODUCTION

A temperature study was performed with RSV2-CAT-B and the control construct (as for Example 5) from 21° C. to 42° C. Transcriptional induction with IPTG was for 30 minutes Extract preparation and CAT assay were as for Example 5. As indicated in Table II below, amplification of CAT activity was greatest for RSV2-CAT-B at 37° C. and the ratio of activity of this construct relative to the control was also high (>5-fold) at this temperature. All quantitative studies were therefore conducted at 37° C. (see Examples 5 and 9). A greater than 5-fold enhancement of CAT expression in RSV2-CAT-B relative to the control was found between 20° C. and 37° C.

TABLE II

| Temperature °C. | Relative CAT-Specific Activity (cpm/μg protein × 10⁻³) | | Ratio RSV2-CAT-B/ Control |
|---|---|---|---|
| | Control | RSV2-CAT-B | |
| 21 | 0.48 | 1.60 | 3.3 |
| 26 | 1.56 | 7.78 | 5.0 |
| 32 | 2.89 | 15.55 | 5.4 |
| 37 | 4.47 | 22.79 | 5.1 |
| 40 | 8.38 | 13.88 | 1.7 |
| 42 | 12.14 | 15.13 | 1.3 |

Cells were grown and the transcriptional induction was performed at the indicated temperature. CAT activity in uninduced cultures of RSV2-CAT-B and controls was $<1 \times 10^3$ cpm/μg protein at all temperatures.

EXAMPLE 7 CONSTRUCTION OF RSV4-CAT-B

To move the intron-CAT cassette closer to the promoter and to determine the effect on product amplification RSV4-CAT-B was constructed. This involved blunt-end cloning the NdeI fragment from RSV2-CAT-B into the SmaI site of pKK223-3 in transcriptional alignment with ptac. The NdeI ends were filled in using Klenow polymerase and the four deoxynucleotide triphosphates, prior to ligation into the SmaI-restricted vector. SmaI digestion followed the ligation step, to enrich for recombinant clones. The NdeI fragment contains 80 nucleotides (nt) of exon I and 20 nt of exon II flanking the tdΔ1-3-CAT-B intron. This brings the intron 689 nt closer to the ptac promoter in RSV4-CAT-B than in RSV2-CAT-B.

EXAMPLE 8 CONSTRUCTION OF RSV5 and RSV5-CAT-B

RSV5, which was derived from RSV2, contains a point mutation within the intron that renders it splicing defective. Isolation of the mutant (pKK223-3-tdΔ1-3-SC79 or RSV5) is described by Chandry and Belfort, Genes and Development 1, 1028 (1987). RSV5-CAT-B was generated by ligating the XbaI CAT fragment from RSV2-CAT-B into XbaI-digested RSV5 and selecting for chloramphenicol resistance.

EXAMPLE 9 THE EFFECT OF PROMOTER DISTANCE AND SPLICING ON OVER-PRODUCTION OF CAT

CAT activity was measured in protein extracts as for Example 5. The data (Table III) show that over-production is further enhanced with proximity to the promoter (compare RSV4-CAT-B with RSV2-CAT-B) and that splicing improves product amplification, but is not absolutely required (compare RSV5-CAT-B with RSV2-CAT-B).

TABLE III

| Time (In hours) | Relative CAT-Specific Activity (cpm/μg protein × 10⁻³) in CAT-B constructs in: | | | |
|---|---|---|---|---|
| | RSV2 | RSV4 | RSV5 | CONTROL* |
| 0 | 1.8 | 3.8 | 0.3 | 0.5 |
| 0.25 | 11.7 | 13.6 | 17.6 | 3.3 |
| 0.5 | 12.6 | 18.6 | 12.4 | 6.7 |
| 1 | 26.4** | 28.3 | 16.5 | 5.7** |
| 1.5 | 23.4 | 29.5 | 22.0 | 8.3 |
| 2 | 49.0 | 50.1 | 42.3 | 13.6 |

*As for Example 5.
**The level of CAT-specific RNA in these two samples was measured using a CAT-specific hybridization probe. The hybridization signal was 4.8 fold greater for RSV2-CAT-B than for the control. CAT levels therefore mirror mRNA levels, which are a reflection of RNA stabilization.

What is claimed is:
1. An RNA stabilization vector, which comprises:
   a cloning vehicle;
   a group I intron inserted into the cloning vehicle; and
   foreign DNA inserted into the intron the resulting foreign DNA-intron fusion not being found in nature.
2. An RNA stabilization vector as in claim 1, wherein the cloning vehicle is a bacterial cloning vehicle.
3. An RNA stabilization vector as in claim 2, wherein the bacterial cloning vehicle is a plasmid.
4. An RNA stabilization vector as in claim 1, wherein the group I intron is the td gene of bacteriophage T4.
5. An RNA stabilization vector as in claim 4, wherein the td gene of bacteriophage T4 is modified by deleting a portion of the intron not contributing to group I secondary structure of the intron.
6. An RNA stabilization vector as in claim 1, wherein the intron is located downstream of a promoter for expressing the foreign DNA.
7. An RNA stabilization vector as in claim 1, further comprising a different restriction enzyme insertion site within the intron.
8. An RNA stabilization vector as in claim 3, wherein the plasmid is pUC9.
9. An RNA stabilization vector as in claim 3, wherein the plasmid is pKK223-3.
10. A method for producing a vector for stabilizing mRNA coding for a gene product, which method comprises inserting a foreign gene coding for the gene product into a group I intron in a cloning vehicle the resulting foreign gene-intron fusion not being found in nature.
11. A method for enhancing the production of a gene product, which comprises:
   inserting a foreign gene into a group I intron in a cloning vehicle the resulting foreign gene-intron fusion not being found in nature;

transcribing the intron with inserted foreign gene in a host cell to form a foreign gene-intron RNA fusion; and translating the foreign gene-intron RNA fusion in the host cell to form the gene product of the foreign gene.

12. A method as in claim 11, wherein the cloning vehicle is a bacterial cloning vehicle.

13. A method as in claim 12, wherein the bacterial cloning vehicle is a plasmid.

14. A method as in claim 11, wherein the group I intron is a td gene of bacteriophage T4.

15. A method as in claim 14, wherein the td gene of bacteriophage T4 is modified by deleting a portion of the intron not contributing to group I secondary structure of the intron.

* * * * *